United States Patent
Nakazawa et al.

(10) Patent No.: US 10,849,918 B2
(45) Date of Patent: Dec. 1, 2020

(54) COMPOSITION FOR OPTIC NERVE PROTECTION

(71) Applicants: TOHOKU TECHNO ARCH CO., LTD., Sendai (JP); WAKAMOTO PHARMACEUTICAL CO., LTD., Tokyo (JP)

(72) Inventors: Toru Nakazawa, Sendai (JP); Naomi Goto, Tokyo (JP)

(73) Assignees: TOHOKU TECHNO ARCH CO., LTD., Sendai (JP); WAKAMOTO PHARMACEUTICAL CO., LTD., Tokyo (JP)

( * ) Notice: Subject to any disclaimer, the term of this patent is extended or adjusted under 35 U.S.C. 154(b) by 229 days.

(21) Appl. No.: 15/744,614

(22) PCT Filed: Jul. 13, 2016

(86) PCT No.: PCT/JP2016/070706
§ 371 (c)(1),
(2) Date: Jan. 12, 2018

(87) PCT Pub. No.: WO2017/010520
PCT Pub. Date: Jan. 19, 2017

(65) Prior Publication Data
US 2018/0207187 A1    Jul. 26, 2018

(30) Foreign Application Priority Data

Jul. 13, 2015   (JP) .................................. 2015-139814

(51) Int. Cl.
| | | |
|---|---|---|
| A61K 31/7048 | (2006.01) | |
| A61K 36/48 | (2006.01) | |
| A23L 33/105 | (2016.01) | |
| A61K 35/747 | (2015.01) | |
| A61P 27/06 | (2006.01) | |

(52) U.S. Cl.
CPC ........ *A61K 31/7048* (2013.01); *A23L 33/105* (2016.08); *A61K 35/747* (2013.01); *A61K 36/48* (2013.01); *A61P 27/06* (2018.01)

(58) Field of Classification Search
CPC ................ A61K 36/48; A61K 2300/00; A61K 31/7048; A61K 35/747; A23L 33/105; A61P 27/06
See application file for complete search history.

(56) References Cited

FOREIGN PATENT DOCUMENTS

| CN | 102639111 A | 8/2012 |
|---|---|---|
| JP | 2009-235069 A | 10/2009 |

OTHER PUBLICATIONS

Chiou Gcy, et al "Effects of some natural flavonoids on retinal function recovery after ischemic insult in the rat" Journal of Ocular Pharmacology and Therapeutics 2004,20(2),pp. 107-113; doi:10.1089/108076804773710777. (Year: 2004).*

Himori, et al., "Possibilities of Drug Treatment and Neuroprotective Treatment for Glaucoma", The Journal of the Japanese Opthalmologists Association, vol. 85, No. 6, pp. 762-765, 2014.

Simazawa, et al., "Brain Science Research using Visual Sense—Endoplasmic Reticulum (ER) Stress and Glaucoma", Brain, vol. 17, No. 4, pp. 459-465, 2014.

Abstracts of Annual Meeting of Pharmaceutical Society of Japan, vol. 132, No. 3, pp. 171, 2012.

Nakatani, et al., "Neuroprotective Effect of Adenosine on Calibrated Optic Nerve Injury in Rats", ARVO Annual Meeting Abstract, vol. 44, May 2003.

Ahn, et al. "Hydroxycinnamic Acids in Crepidiastrum denticulatum Protect Oxidative Stress-Induced Retinal Damage" Journal of Agricultural and Food Chemistry, vol. 62, No. 6, pp. 1310-1323, 2014.

Oku, et al., "Roles of Adenosine in the Retina, Mainly the Effects on Retinal Vessels and Neuroprotection", Neuro-opthalmol. Japan, vol. 22, No. 3, pp. 418-424, 2005.

Tomita, et al., "Prospects of Glaucoma and Intraocular Pressure", Opthamology, vol. 40, pp. 251-273, 1998.

Office Action dated May 28, 2020 issued in corresponding Taiwanese Application No. 105122025, 10 pages.

Xiaoting, et al., "Effect of Hesperidin on Expression of Inducible Nitric Oxide Synthase in Cultured Rabbit Retinal Pigment Epithelial Cells", Retinal Degenerative Diseases, pp. 192-201, 2010.

"Diabetes and eye disease", Newsletter of Mackey Memorial Hospital, 313: http://www.mmh.org.tw/MackayInfo2/article/B313/73, 2011, 6 pages.

Office Action dated Apr. 10, 2020 issued in corresponding Chinese Application No. 201680042449.1, 15 pages.

Shi, et al., "Hesperidin Prevents Retinal and Plasma Abnormalities in Streptozotocin-Induced Diabetic Rats", Molecules, vol. 17, pp. 12868-12881, 2012.

Tsinghua, "Integrated Traditional Chinese and Western Ophthalmology", China Publishing House of Traditional Chinese Medicine, pp. 676-677, Jan. 2010.

Ping_Yu, et al., "Common Eye Diseases in Middle-Aged and Elderly", Kim Dun Press, p. 105, Oct. 2014.

Lee, "Adhesion and Proliferation Behavior of Retinal Pigment Epithelial Cells on Hesperidin/PLGA Films" Polymer Korea, vol. 38, No. 1, Jan. 2014. pp. 24-30.

(Continued)

*Primary Examiner* — Aaron J Kosar
(74) *Attorney, Agent, or Firm* — Nath, Goldberg & Meyer; Joshua B. Goldberg

(57) ABSTRACT

A composition for optic nerve cell protection, for preventing or treating glaucoma, for suppressing retinal ganglion cell death, or for delaying a progression of visual acuity loss of human contains at least one selected from the group consisting of products obtained by steaming and drying wheat, defatted wheat germ, defatted rice germ, defatted soybean, fermented grape, hesperidin, lactic acid bacterium *Lactobacillus salivarius*, wild grape, Tamarind, Haskap, pomegranate seeds, licorice powder, and cinnamon powder.

18 Claims, 6 Drawing Sheets

(56) References Cited

OTHER PUBLICATIONS

Majumdar, et al., "Solubility, Stability, Physicochemical Characteristics and In Vitro Ocular Tissue Permeability of Hesperidin: a Natural Bioflavonoid", A Natural Bioflavonoid, vol. 26, No. 5, pp. 1217-1225, 2009.
Chinese Office Action dated Sep. 10, 2020, in corresponding CN application No. 201680042449.1 with English translation.

* cited by examiner

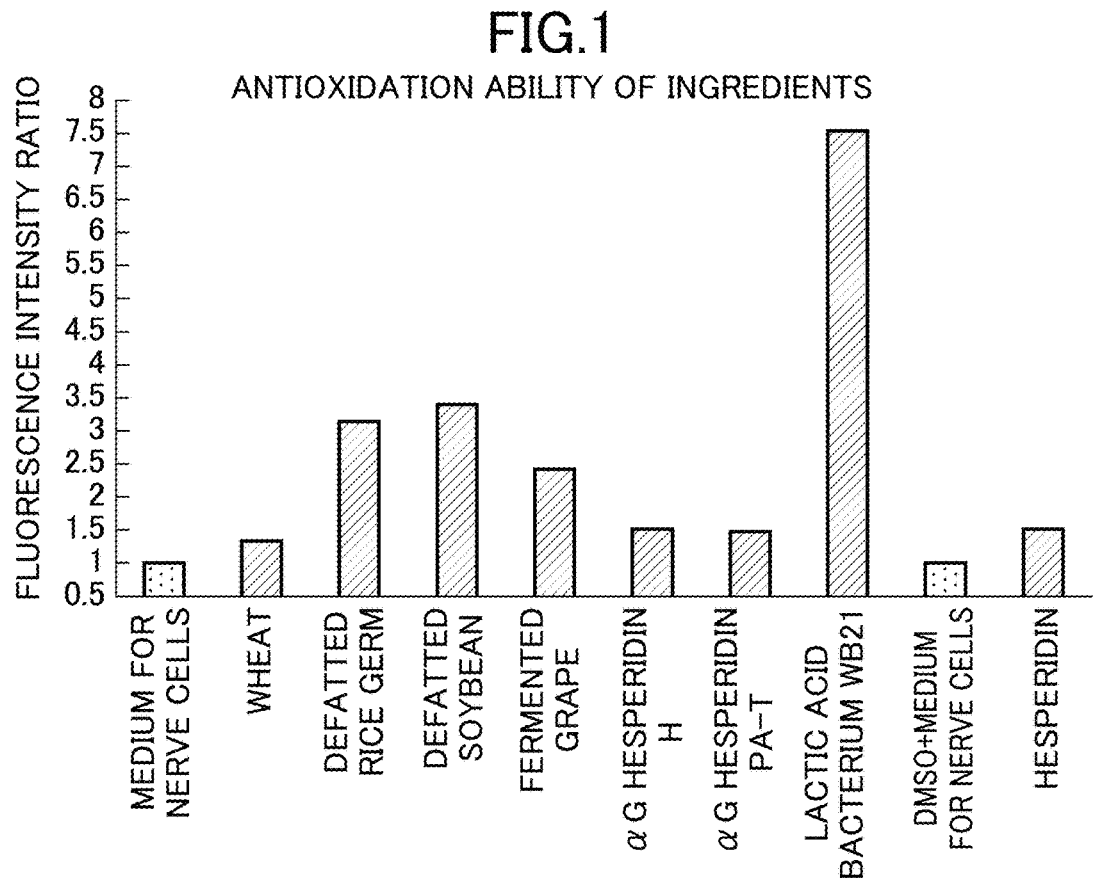
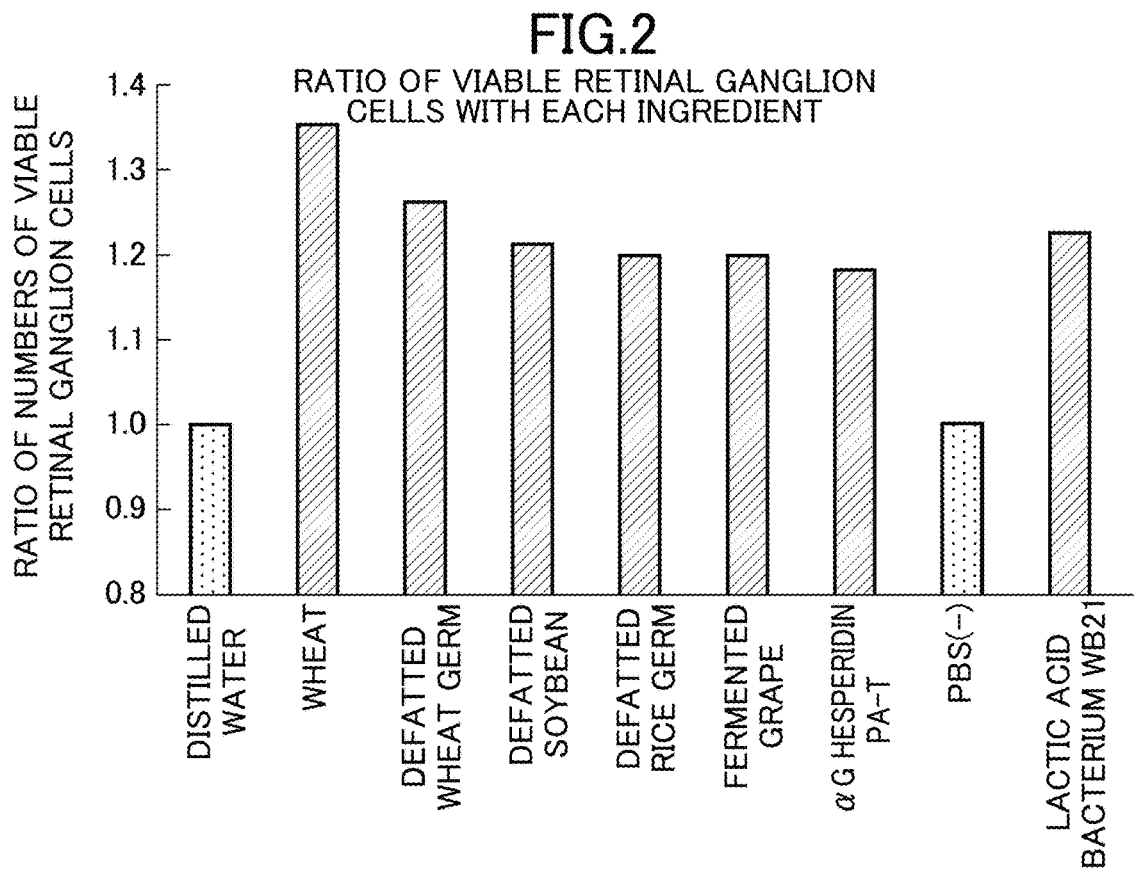

FIG.9
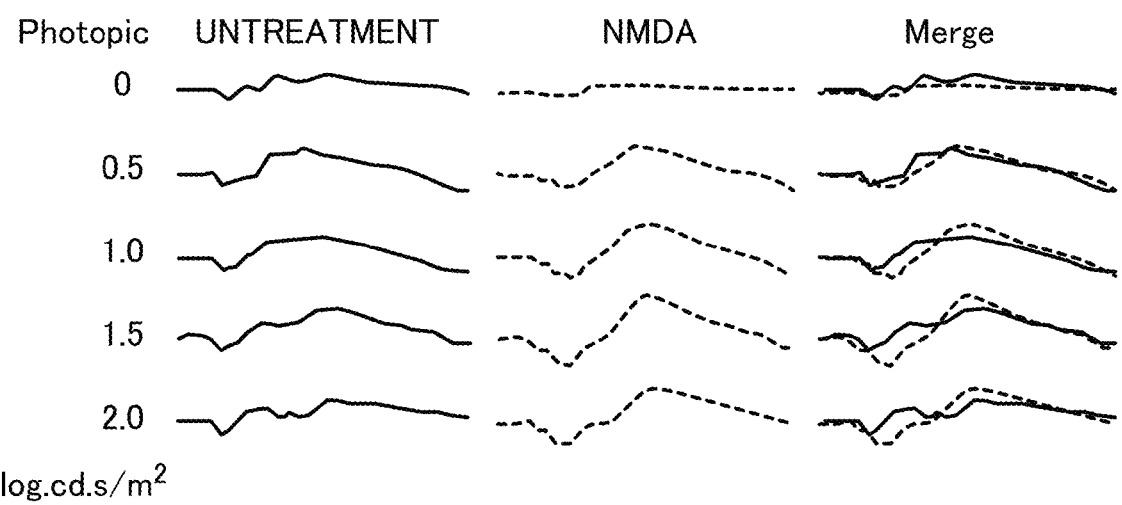
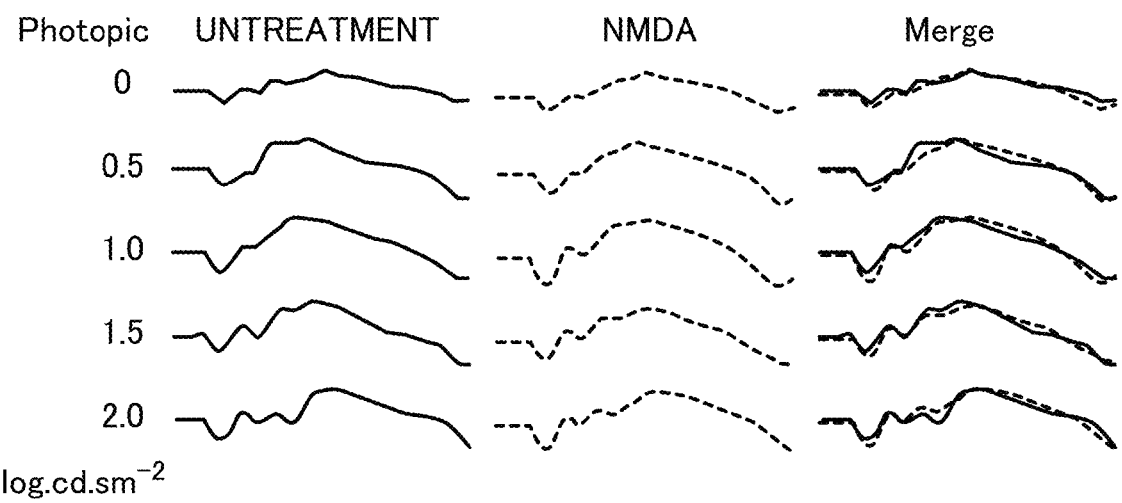

COMPOSITION FOR OPTIC NERVE PROTECTION

This is a National Phase Application filed under 35 U.S.C. 371 as a national stage of PCT/JP2016/070706, filed Jul. 13, 2016, an application claiming the benefit of Japanese Application No. 2015-139814, filed Jul. 13, 2015, the content of each of which is hereby incorporated by reference in its entirety.

TECHNICAL FIELD

The present invention relates to a composition for optic nerve protection.

BACKGROUND ART

Retinal ganglion cells located in the innermost layer of the retina are nerve cells included in retinal cells, and play roles in collecting stimuli from photoreceptor cells and transmitting the stimuli to the optic nerve. A failure in this series of transduction pathway leads to visual function deterioration.

Glaucoma, which occurs in 5% of Japanese who are 40 years old and older and is the No. 1 cause of vision loss, is a disease causing the visual field impairment, too. As the final pathological condition, the optic nerve is damaged due to the death of retinal ganglion cells.

Hence, there has been a widespread thought that if a treatment for preventing or minimizing the retinal ganglion cell death is conceived, it leads to the glaucoma therapy (Ganka (Ophthalmology), 40, 251-273).

However, at present, the only evidence-based therapeutic method against glaucoma is a treatment for reducing the intraocular pressure by employing drugs, lasers, and/or operative surgery. As proposed in Collaborative Normal-Tension Glaucoma Study, the treatments have been performed which focus on reducing the intraocular pressure by 30% to keep the visual field. The high-quality therapy has been spread because of the developments of many intraocular pressure-lowering drugs, enhancing the therapeutic effect by the action of the intraocular pressure reduction. Nevertheless, the disease type of many Japanese glaucoma patients is normal tension glaucoma in which the intraocular pressure falls within a normal range. Accordingly, there are many patients who have difficulty in achieving the 30% intraocular pressure reduction, and cases from which a progression of the visual field impairment is observed even though the intraocular pressure is sufficiently low. Thus, there is a limit in the glaucoma therapy which only reduces the intraocular pressure as currently performed. It has been said that treatments need to focus on and deal with other risk factors than intraocular pressure (The Journal of the Japanese Opthalmologists Association, 85, no. 6, 762-765).

On the other hand, it is speculated that the malfunctioning of the antioxidation system in the entire body and the retinal optic nerve is involved as one cause of the pathological progression of glaucoma. The nerve protection effect by an antioxidative substance against glaucoma optic neuropathy has been demonstrated, and the development of novel nerve protection drugs utilizing the antioxidation as an application of an antioxidative drug has been expected (Atarashii Ganka (New Ophthalmology—Journal of the eye), 31, no. 5, 699-700). However, no effective therapeutic method has been established yet currently.

Further, recently, attention has been focused on the involvement of endoplasmic reticulum stress in glaucoma. It has been revealed that various types of cellular stresses induce endoplasmic reticulum stresses before retinal ganglion cells die. In addition, it has been suggested that excessive endoplasmic reticulum stresses are associated with the onset and progression of neurological diseases such as Alzheimer's disease, amyotrophic lateral sclerosis, and Parkinson's disease (Brain 21, 17, No. 4, 459-465). However, no effective therapeutic method against these has been established yet currently, either.

SUMMARY OF INVENTION

Technical Problems

An object of the present invention is to provide effective means for protecting optic nerve cells, and to provide a composition for preventing or treating a disease or disorder associated with optic nerve cell death, particularly glaucoma.

Solution to Problems

The present inventors have intensively studied in various tests by oral administration or intraocular administration using a glaucoma pathological model of an optic nerve crush injury murine model and a glaucoma pathological model that induces cell death by NMDA administration through a cytotoxic mechanism different from that of the optic nerve crush injury murine model. As a result, the inventors have found that: 13 types of base materials including products obtained by steaming and drying wheat, defatted wheat germ, defatted rice germ, defatted soybean, fermented grape, hesperidin, lactic acid bacterium *Lactobacillus salivarius* (hereinafter abbreviated as "lactic acid bacterium LS"), wild grape, Tamarind, Haskap, pomegranate seeds, licorice powder, and cinnamon powder each alone have an excellent protection effect on the death of retinal ganglion cells; and 7 types of base materials including wild grape, Tamarind, Haskap, pomegranate seeds, licorice powder, products obtained by steaming and drying wheat, and cinnamon powder each alone have an excellent action of suppressing endoplasmic reticulum stress.

Specifically, the present invention provides the following compositions:

[1] A composition for optic nerve cell protection, comprising at least one active ingredient selected from the group consisting of products obtained by steaming and drying wheat, defatted wheat germ, defatted rice germ, defatted soybean, fermented grape, hesperidin, and lactic acid bacterium *Lactobacillus salivarius*.

[2] A composition for preventing or treating glaucoma, comprising at least one active ingredient selected from the group consisting of products obtained by steaming and drying wheat, defatted wheat germ, defatted rice germ, defatted soybean, fermented grape, hesperidin, and lactic acid bacterium *Lactobacillus salivarius*.

[3] A composition for suppressing optic nerve cell death, suppressing retinal ganglion cell death, or delaying a progression of visual acuity loss of human, comprising at least one active ingredient selected from the group consisting of products obtained by steaming and drying wheat, defatted wheat germ, defatted rice germ, defatted soybean, fermented grape, hesperidin, and lactic acid bacterium *Lactobacillus salivarius*.

[4] A composition for optic nerve cell protection, comprising at least one active ingredient selected from the group consisting of wild grape, Tamarind, Haskap, pomegranate seeds, licorice powder, and cinnamon powder.

[5] A composition for preventing or treating glaucoma, comprising at least one active ingredient selected from the group consisting of wild grape, Tamarind, Haskap, pomegranate seeds, licorice powder, and cinnamon powder.

[6] A composition for suppressing optic nerve cell death, suppressing retinal ganglion cell death, or delaying a progression of visual acuity loss of human, comprising at least one active ingredient selected from the group consisting of wild grape, Tamarind, Haskap, pomegranate seeds, licorice powder, and cinnamon powder.

[7] A composition for suppressing endoplasmic reticulum stress, comprising at least one active ingredient selected from the group consisting of wild grape, Tamarind, Haskap, pomegranate seeds, licorice powder, products obtained by steaming and drying wheat, and cinnamon powder.

[8] The composition according to any one of claims 1 to 7, which is a drug administered orally or intraocularly.

[9] The composition according to any one of claims 1 to 7, which is in a form of food.

[10] The composition according to claim 9, comprising an indication stating that the composition has at least one function selected from the group consisting of an antioxidation activity, suppressing endoplasmic reticulum stress, suppressing optic nerve cell death, suppressing retinal ganglion cell death, suppressing a progression of visual field of human, and suppressing a progression of visual acuity loss of human.

Advantageous Effects of Invention

The composition for optic nerve protection of the present invention makes it possible to effectively prevent or treat eye diseases associated with optic nerve cell death, particularly glaucoma.

BRIEF DESCRIPTION OF DRAWINGS

FIG. 1 shows the result of Test 1 (antioxidation ability of ingredients).
FIG. 2 shows the result of Test 2 (ratio of viable retinal ganglion cells with each ingredient).
FIG. 9 shows the result of Test 7 (evaluation of electrophysiological function of intraocularly administered enzyme-treated hesperidin).

DESCRIPTION OF EMBODIMENTS

[Active Ingredients]

Figure 3:
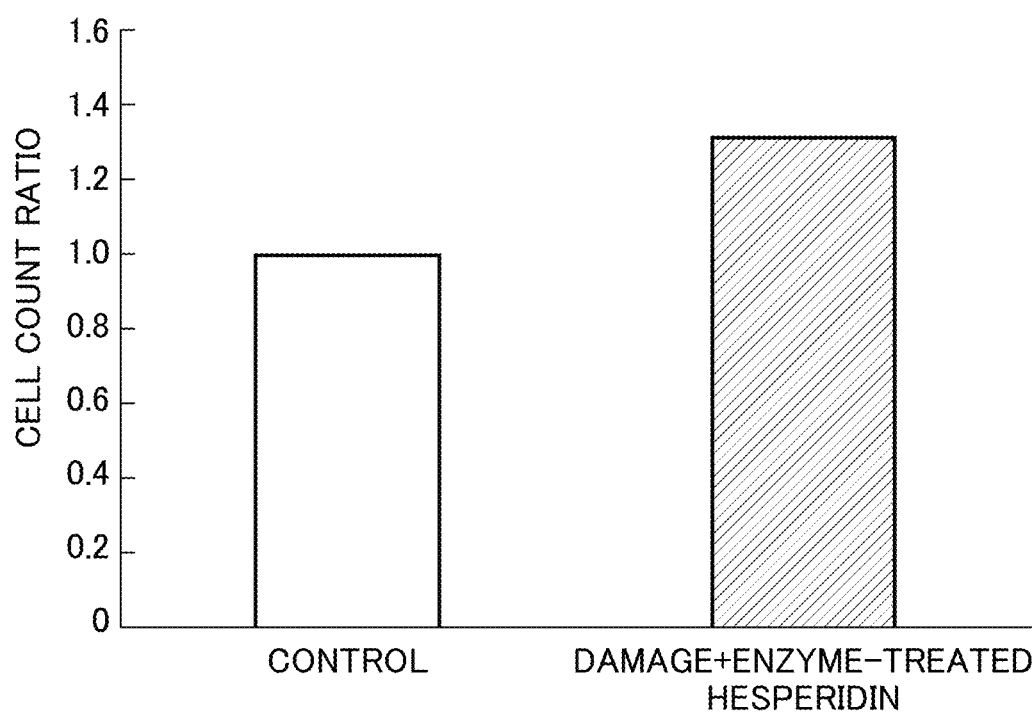
FIG. 3 shows the result of Test 3 (ratio of viable retinal ganglion cells by enzyme-treated hesperidin oral administration).

The present invention contains, as an active ingredient at least one selected from the group consisting of products obtained by steaming and drying wheat (*Triticum*), defatted wheat germ, defatted rice (*Oryza*) germ, defatted soybean (*Glycine max*), fermented grape (*Vitis*), hesperidin, lactic acid bacterium *Lactobacillus salivarius*, wild grape (*Ampelopsis glandulosa* var. *heterophylla*), Tamarind (*Tamarindus indica*), Haskap (*Lonicera caerulea*), pomegranate (*Punica granatum*) seeds, licorice (*Glycyrrhiza uralensis, G. glabra*) powder, cinnamon (*Cinnamomum cassia*) powder, extraction liquids thereof, and combinations thereof.

The products obtained by steaming and drying wheat can be produced according to known methods, or commercially available products can also be used. Examples of the commercially available products include ones under the product name of "Koujimugi (registered trademark) ST" (manufactured by Fresh Food Service Co., Ltd.) and the like.

The defatted wheat germ can be produced according to known methods, or commercially available products can also be used. Examples of the commercially available products include ones under the product name of "Dasshi Komugi Haiga Furawah TYPE-R" (manufactured by Koyo Mercantile Co., Ltd.) and the like.

The defatted rice germ can be produced according to known methods, or commercially available products can also be used. As a known method, lipophilic fractions are separated from a rice germ (which is thus defatted) by using an organic solvent such as n-hexane so that the target product can be obtained. The organic solvent can be removed through vaporization by heating.

The defatted soybean can be produced according to known methods, or commercially available products can also be used. Examples of the commercially available products include ones under the product name of "Dasshi Daizu HAIPURO" (manufactured by J-Oil Mills, Inc.) and the like.

The fermented grape can be produced according to known methods, or commercially available products can also be used. As a known method, for example, the fruit of a grape with the outer skin is crushed, and fermented with the yeast on the skin. Only the fruit skin and seed of a grape may be fermented. Additionally, a yeast or a lactic acid bacterium may be added. The crushed fruit after the fermentation can be used, or an extract therefrom can also be used. The variety of the grape is not particularly limited, but a Koshu variety is suitable. The commercially available products include ones under the product name of "Fermented Grape Food" (manufactured by Vino Science Japan) and the like.

The hesperidin and enzyme-treated hesperidin (enzymatically hesperidin glycosylated) can be produced according to known methods, or commercially available products can also be used. The commercially available products of the hesperidin include ones under the product name of "Hesperidin" (manufactured by Alps Pharmaceutical Industry Co., Ltd.) and the like. The commercially available products of the enzyme-treated hesperidin include ones under the product names of "αG Hesperidin H", "αG-Hesperidin PA", "αG-Hesperidin PA-T" (manufactured by Toyo Sugar Refining Co., Ltd., Glico Nutrition Co., Ltd.), and the like.

As the lactic acid bacterium LS, it is possible to suitably use, for example, living cells, wet cells, dry cells, dead cells, culture supernatants, cultures containing medium ingredients, frozen dried cells, bulked products thereof, or the like. As the lactic acid bacterium LS, it is possible to use, for example, *Lactobacillus salivarius WB*21 strain (Accession No. FERM BP-7792) deposited by Wakamoto Pharmaceutical Co., Ltd.

As the wild grape, it is possible to suitably use, for example, the fruit with the outer skin, pulp, branch, leaf, dried materials thereof, extracts thereof, or the like. Examples of commercially available products thereof include ones under the product name of "Nobudou Kansou Ekisu F" (manufactured by Maruzen Pharmaceuticals Co., Ltd.) and the like.

As the Tamarind, it is possible to suitably use, for example, the fruit with the outer skin, pulp, the seed or seed coat in the fruit, dried materials thereof, extracts thereof, or the like. Examples of commercially available products thereof include ones under the product name of "Indian date extract powder MF" (manufactured by Maruzen Pharmaceuticals Co., Ltd.) and the like.

As the Haskap, it is possible to suitably use, for example, the fruit with the outer skin, pulp, dried materials thereof, extracts thereof, or the like. Examples of commercially available products thereof include ones under the product name of "Haskap Powder S" (manufactured by Nippon Shinyaku Co., Ltd.) and the like.

As the pomegranate seeds, it is possible to suitably use, for example, the seeds, dried materials thereof, extracts thereof, or the like. Examples of commercially available products thereof include ones under the product name of "Zakuro shusi Kansou Ekisu" (manufactured by Ask Intercity Co., Ltd.) and the like.

As the licorice powder, it is possible to suitably use, for example, the root, stolon, dried materials thereof, extracts thereof, or the like. Examples of commercially available products thereof include ones under the product name of "Shokuhin Genryou yo Kanzoumatsu" (manufactured by Nippon Funmatsu Yakuhin Co., Ltd.) and the like.

As the cinnamon powder, it is possible to suitably use, for example, the bark, dried materials thereof, extracts thereof, or the like. Examples of commercially available products thereof include ones under the product name of "Shokuhin Genryou yo Keihimatsu" (manufactured by Nippon Funmatsu Yakuhin Co., Ltd.) and the like.

Each of the extraction liquids can be prepared, for example, by introducing the active ingredient into a pharmacologically acceptable extraction solvent such as water or ethanol so that at least one ingredient included in the active ingredient can leach out.

The amount of the product obtained by steaming and drying wheat blended in the composition of the present invention is preferably 0.05 to 100 parts by mass relative to 100 parts by mass of the composition.

The amount of the defatted wheat germ blended in the composition of the present invention is preferably 0.05 to 100 parts by mass, more preferably 0.5 to 100 parts by mass, and further preferably 5 to 100 parts by mass, relative to 100 parts by mass of the composition.

The amount of the defatted rice germ blended in the composition of the present invention is preferably 0.05 to 100 parts by mass, more preferably 0.5 to 100 parts by mass, and further preferably 5 to 100 parts by mass, relative to 100 parts by mass of the composition.

The defatted soybean in the composition of the present invention is in an amount of preferably 0.05 to 100 parts by mass, more preferably 0.5 to 100 parts by mass, and further preferably 5 to 100 parts by mass, relative to 100 parts by mass of the composition.

The amount of the fermented grape blended in the composition of the present invention is preferably 0.05 to 100 parts by mass, and more preferably 0.5 to 100 parts by mass, relative to 100 parts by mass of the composition.

The amount of the hesperidin blended in the composition of the present invention is preferably 0.01 to 100 parts by mass relative to 100 parts by mass of the composition.

The amount of the enzyme-treated hesperidin blended in the composition of the present invention is preferably 0.025 to 100 parts by mass relative to 100 parts by mass of the composition.

The lactic acid bacterium LS is preferably blended into the composition of the present invention such that the number of lactic acid bacterial cells is preferably 1 million to 100 trillion per 100 parts by mass of the composition.

The amount of the wild grape blended in the composition of the present invention is preferably 0.005 to 100 parts by mass, and more preferably 0.05 to 100 parts by mass, relative to 100 parts by mass of the composition.

The amount of the Tamarind blended in the composition of the present invention is preferably 0.0001 to 100 parts by mass, and more preferably 0.005 to 100 parts by mass, relative to 100 parts by mass of the composition.

The amount of the Haskap blended in the composition of the present invention is preferably 0.005 to 100 parts by mass, and more preferably 0.05 to 100 parts by mass, relative to 100 parts by mass of the composition.

The amount of the pomegranate seeds blended in the composition of the present invention is preferably 0.005 to 100 parts by mass, and more preferably 0.05 to 100 parts by mass, relative to 100 parts by mass of the composition.

The amount of the licorice powder blended in the composition of the present invention is preferably 0.005 to 100 parts by mass, and more preferably 0.05 to 100 parts by mass, relative to 100 parts by mass of the composition.

The amount of the cinnamon powder blended in the composition of the present invention is preferably 0.005 to 100 parts by mass, and more preferably 0.05 to 100 parts by mass, relative to 100 parts by mass of the composition.

The composition of the present invention can be used as a food or pharmaceutical product for preventing or treating glaucoma—particularly one caused by optic nerve cell death.

As the food form, health foods or foods with nutrient function claims such as supplements can also be prepared by further blending a saccharide, a lipid, a protein, an amino acid, vitamins, other minerals, royal jelly, propolis, honey, dietary fibers, astaxanthin, EPA, DHA, lactoferrin, *agaricus*, chitin, chitosan, capsaicin, a polyphenol, a carotenoid, a fatty acid, a mucopolysaccharide, a coenzyme, an antioxidative substance, or the like.

The form of the food composition is not particularly limited. Examples thereof include tablets; capsules; powders to be dissolved in water, milk, or the like to be drunk; beverages; confectioneries; cold sweets; and the like.

As the pharmaceutical product form, the dosage form can be prepared by mixing a pharmacologically acceptable carrier or diluent, for example, a cellulose derivative such as carboxymethyl cellulose or ethyl cellulose; a starch such as potato starch or corn starch; a sugar such as milk sugar or sucrose; a vegetable oil such as peanut oil, corn oil, or sesame oil; polyethylene glycol, alginic acid, gelatin, talc, or the like. The dosage form includes orally administered preparations such as tablets, capsules, granules, and powders; preparations for oral cavity application such as tablets for oral cavity and semi-solid preparations for oral cavity; injections; eye drops; preparations for rectum application such as suppositories and enema preparations; preparations for skin application such as ointments and patches; crude-drug related preparations such as extracts, pills, and decoctions; and the like. The pharmaceutical product of the present invention can be orally or parenterally administered (for example, administered into eyes or vitreous body).

It is appropriate to continuously take the composition of the present invention every day. When an adult having a body weight of approximately 60 kg takes the composition of the present invention, a desirable single intake amount in terms of the active ingredient amount is preferably 0.0001 to 3.3 g, and more preferably 0.0003 to 3.3 g. When an adult having a body weight of approximately 60 kg takes the composition of the present invention, the intake amount per day in terms of the active ingredient amount is desirably 0.0003 to 10 g, and more preferably 0.001 to 10 g.

Example

Test 1. Study of Antioxidation Ability

Isolated retinal cells from mice were cultured in a medium for nerve cells blended with each ingredient from which optic nerve protection was expected. Based on the presence or absence of an antioxidation ability of each ingredient, the effect on the isolated retinal cells was verified.

[Materials and Method]

<Materials>

As the ingredients from which optic nerve protection was expected, the following substances or extraction liquids thereof were used in the test.

A product obtained by steaming and drying wheat (product name: "Koujimugi(registered trademark) ST", manufactured by Fresh Food Service Co., Ltd. (hereinafter referred to as "wheat")); defatted rice germ (this target product can be obtained by separating lipophilic fractions from a rice germ (which is thus defatted) by using an organic solvent such as n-hexane. The organic solvent is removed through vaporization by heating); defatted soybean (product name: "Dasshi Daizu HAIPURO", manufactured by J-Oil Mills, Inc.); fermented grape (product name: "Fermented Grape Food", Vino Science Japan); hesperidin (product name: "Hesperidin", Alps Pharmaceutical Industry Co., Ltd.); enzyme-treated hesperidin (product name: "αG-Hesperidin H", product name: "αG-Hesperidin PA", Glico Nutrition Co., Ltd.); lactic acid bacterium *Lactobacillus salivarius* WB21 strain (hereinafter abbreviated as "lactic acid bacterium WB21") (Accession No. FERM BP-7792)

Test cells: isolated retinal cells from adult mice

Test medium: medium for nerve cells (composition: Neurobasal-A Medium (1×), Liquid (Life Technologies); B-27 (registered trademark) supplement Minus AO (50×), Liquid (Life Technologies) (hereinafter abbreviated as "B-27 supplement (AO-)"), 2%; gentamicin, 12 μg/mL; L-glutamine, 2 mM; Insulin, 1 μg/mL)

Medium for adjusting cell count (composition: Neurobasal-A Medium (1×), Liquid (Life Technologies); Gentamicin, 0.25 mg/mL; L-glutamin, 0.5 mM; insulin, 0.005 mg/mL; B-27 supplement (AO-), 2%

<Method>

1. Verification of Antioxidation Ability of Each Health Food Ingredient Candidate by Using Isolated Retinal Cells from Adult Mice The isolated retinal cells from adult mice were cultured on the medium for nerve cells supplemented with the B-27 supplement (AO-), and the condition was selected such that the cells died in a short period. The B-27 supplement (AO-) is a B-27(registered trademark) supplement without five antioxidative substances (vitamin E, vitamin E acetate, superoxide dismutase, catalase, and glutathione) which influence the research for damage by free radicals to neurons. The viable cells were analyzed by AlamarBlue(trademark) assay capable of quantifying cell viability. AlamarBlue (Invitrogen, product number: DAL1100) is reduced by viable cells, and changes the color from Prussian blue in the oxidized form to fluorescent red in the reduced form.

The experiment was conducted according to the following procedure. The number of samples in each group was 4.

(1) The isolated retinal cells from adult mice were obtained using gentleMACS (Miltenyi Biotec K. K.) and Neural Tissue Dissociation Kit (P) (Miltenyi Biotec K. K.) as follows.

1) The mice (male C57BL/6 strain mice, 8-11 weeks old) were euthanized, and the eyeballs were excised. The retinal tissues were collected into HBSS (-) with phenol red (Wako Pure Chemical Industries, Ltd., Code No. 084-08345).

2) After 1.9 ml of Buffer X and 50 μl of Enzyme P of Neural Tissue Dissociation Kit (P) and four retinas were introduced in gentleMACS Tube, the mixture was set in MACSmix Tube Rotator and stirred in an incubator of 37° C. and 5% $CO_2$ at the slowest speed for 5 minutes.

3) After the gentleMACS Octo Dissociator program "m_brain_01" was run, the mixture was set in MACSmix (trademark) and stirred in the incubator of 37° C. and 5% $CO_2$ at the slowest speed for 3 minutes.

4) After the gentleMACS program "m_brain_02" was run, a liquid mixture of 20 μl of Buffer Y and 10 μl of Enzyme A was added. The resultant was set in MACSmix and stirred in the incubator of 37° C. and 5% $CO_2$ at the slowest speed for 5 minutes.

5) After the gentleMACS Octo Dissociator program "m_brain_03" was run, the resultant was set in MACSmix Tube Rotator and stirred in the incubator of 37° C. and 5% $CO_2$ at the slowest speed for 5 minutes.

6) The solution was filtered through Cell Strainer (φ: 40 μm), centrifuged, and suspended in the medium for nerve cells.

7) A portion of the cell solution was separated, and viable cells not stained with a trypan blue dye were counted using a hemocytometer.

(2) Based on the counting result, the isolated retinal cells from adult mice were diluted and seeded in each well of a 96-well plate such that there were $1.8 \times 10^5$ viable cells in 50 μL of the medium for adjusting cell count/well. The cells were cultured in the incubator of 5% $CO_2$ at 37° C. for 15 minutes for the adhesion to the bottom surface of each well of the 96-well plate.

(3) In experimental groups, each ingredient prepared using the medium for nerve cells as shown in Table 1 was added in an amount of 504 to each well in (2); in each control group of wheat, defatted rice germ, defatted soybean, fermented grape, αG-hesperidin H, αG-hesperidin PA-T, and lactic acid bacterium WB21, only the medium for nerve cells was added likewise; for a control group of hesperidin, dimethyl sulfoxide (Wako Pure Chemical Industries, Ltd.) diluted to the final concentration of 0.1% with the medium for nerve cells was added likewise. These resultants were cultured in the incubator of 37° C. and 5% $CO_2$ for 2 hours.

| Ingredients | Concentration (w/v) | Preparation method |
|---|---|---|
| Wheat | 0.05 | Wheat was suspended in the medium for nerve cells at the concentration in the left column, and rotated with a rotator for 30 minutes. Then, the supernatant was filtered through a filter. |

-continued

| Ingredients | Concentration (w/v) | Preparation method |
|---|---|---|
| | | Thus, an extraction liquid was obtained. |
| Defatted rice germ | 5.00 | Defatted rice germ was suspended in the medium for nerve cells at the concentration in the left column, and rotated with a rotator for 30 minutes. Then, the supernatant was filtered through a filter. Thus, an extraction liquid was obtained. |
| Defatted soybean | 5.00 | Defatted soybean was suspended in the medium for nerve cells at the concentration in the left column, and rotated with a rotator for 30 minutes. Then, the supernatant was filtered through a filter. Thus, an extraction liquid was obtained. |
| Fermented grape | 0.50 | Fermented grape was suspended in the medium for nerve cells at the concentration in the left column, and rotated with a rotator for 30 minutes. Then, the supernatant was filtered through a filter. Thus, an extraction liquid was obtained. |
| Hesperidin | 0.01 | Hesperidin was dissolved in dimethyl sulfoxide to a concentration of 10%. Then, the concentration was adjusted to the concentration in the left column with the medium for nerve cells. |
| αG-Hesperidin H | 0.05 | αG-hesperidin H was dissolved in the medium for nerve cells at the concentration in the left column. |
| αG-Hesperidin PA-T | 0.50 | αG-hesperidin PA-T was dissolved in the medium for nerve cells at the concentration in the left column. |
| Lactic acid bacterium WB21 | 0.50 | Lactic acid bacterium WB21 was suspended in the medium for nerve cells at the concentration in the left column, and rotated with a rotator for 30 minutes. Then, the supernatant was filtered through a filter. Thus, an extraction liquid was obtained. |

(4) AlamarBlue in an amount of 10 μL was added to each well in (3). The chromogenic reaction was carried out in the incubator of 5% $CO_2$ at 37° C. for approximately 24 hours.

(5) After the chromogenic reaction, the fluorescence intensity (excitation wavelength: 544-570 nm, measurement wavelength: 590 nm) was measured to evaluate the number of viable cells.

As a result, FIG. 1 shows the ratio of the measurement value of each fluorescence intensity in the eight experimental groups, given that the measurement values of the fluorescence intensities in the control groups are taken as 1. In all of the eight experimental groups, the measurement values were higher than those of the control groups. Accordingly, the number of viable cells in the experimental groups was larger than the number of viable cells in the control groups. This revealed that each ingredient shown in Table 1 had an antioxidation ability. Thus, it can be presumed that each ingredient shown in Table 1 has an optic nerve protection effect.

Test 2. Study of Optic Nerve Protection Effect in Murine Glaucoma Model

The nerve protection effect of each ingredient was verified by using a rodent glaucoma pathological model of an optic nerve crush injury murine model.

[Materials and Method]

<Materials>

Ingredients

As the ingredients from which optic nerve protection was expected, the following substances were used in the test.

Enzyme-treated hesperidin (product name: "αG-Hesperidin PA-T", manufactured by Glico Nutrition Co., Ltd.); fermented grape (product name: "Fermented Grape Food", Vino Science Japan); a product obtained by steaming and drying wheat (product name: "Koujimugi(registered trademark)ST", manufactured by Fresh Food Service Co., Ltd. (hereinafter referred to as "wheat")); defatted wheat germ (product name: "Dasshi Komugi Haiga Furawah TYPE-R", manufactured by Koyo Mercantile Co., Ltd.; defatted rice germ (this target product can be obtained by separating lipophilic fractions from a rice germ (which is thus defatted) by using a n-hexane organic solvent. The organic solvent is removed through vaporization by heating); defatted soybean (product name: "Dasshi Daizu HAIPURO", manufactured by J-Oil Mills, Inc.); lactic acid bacterium *Lactobacillus salivarius* WB21 strain (hereinafter abbreviated as "lactic acid bacterium WB21") (Accession No. FERM BP-7792))

Test animal: male C57BL/6 strain mice, 9-12 weeks old, each approximately 25 g

The experiment was conducted according to the following method. The number of samples in each group was 8.

<Method>

(1) To label retinal ganglion cells, one week before optic nerve crush surgery, 1% Fluoro-Gold (Fluorochrome, LLC) was injected into the superior colliculus of the mouse brain under anesthesia.

(2) To the mice in the experimental groups, each ingredient prepared as shown in Table 2 was orally administered at a dosage as shown in Table 2 once a day from one week before the optic nerve crush treatment; to the mice in the control groups, 100 μL of distilled water or phosphate-buffered saline (containing no Ca or Mg, pH: 7.4, hereinafter abbreviated as "PBS(−)") was administered likewise.

TABLE 2

| Dosage/day | Ingredients | Preparation method |
|---|---|---|
| 100 μL/mouse | Wheat | 200 mg was suspended in 1.2 ml of distilled water, rotated with a rotator for 20 minutes, and then centrifuged to prepare the supernatant as an extraction liquid (control: distilled water) |
| | Defatted wheat germ | 50 mg was suspended in 1 ml of distilled water (control: distilled water) |
| | Defatted rice germ | 50 mg was suspended in 1 ml of distilled water (control: distilled water) |

TABLE 2-continued

| Dosage/day | Ingredients | Preparation method |
|---|---|---|
| | Defatted soybean | 50 mg was suspended in 1 ml of distilled water (control: distilled water) |
| | Fermented grape | 75 mg was suspended in 1 ml of distilled water (control: distilled water) |
| | αG-Hesperidin PA-T | 125 mg was suspended in 1 ml of distilled water (control: distilled water) |
| | Lactic acid bacterium WB21 | 500 mg was suspended in 1 ml of PBS(−) (control: PBS(−)) |

(3) The optic nerve crush treatment on the mice was performed under anesthesia by administering ketamine (100 mg/kg) and xylazine (5 mg/kg). The optic nerve crush treatment was performed on only single eyes, and the fellow eyes were untreated. After the optic nerve crush treatment was completed, an antibacterial ophthalmic ointment was instilled to the eyes of the mice.

(4) From the following day of the optic nerve crush treatment, each ingredient in Table 2 was orally administered to the mice in the experimental groups once a day; to the mice in the control groups, 100 μL of distilled water or PBS(−) was administered likewise.

(5) On Day 10 after the optic nerve crush treatment, the retinas were excised from the mice. The retinas were fixed with 4% paraformaldehyde phosphate buffer solution (Wako Pure Chemical Industries, Ltd.), and then a fluorescent mounting agent VECTASHIELD Mounting Medium (Vector Laboratories, Product Code: H-1000) was mounted thereon.

(6) Images of 12 sites each of 500 square pixels on one retina were captured.

(7) The number of cells labeled with Fluoro-Gold was counted to obtain an average number at the 12 sites. This was regarded as the number of viable retinal ganglion cells per square millimeter. The average was obtained for each group.

As a result, FIG. 2 shows the ratios of the average numbers of viable retinal ganglion cells per square millimeter in the experimental groups, given that the average numbers of viable retinal ganglion cells per square millimeter in the control groups are taken as 1. The numbers of viable retinal ganglion cells in the experimental groups were larger than the numbers of viable retinal ganglion cells per square millimeter in the control groups. To put it differently, it was revealed that each ingredient shown in Table 2 suppressed the retinal ganglion cell death induced by the optic nerve crush injury. It was verified that all the ingredients tested had an optic nerve protection effect.

Test 3. Study of Effect of Protecting Retinal Ganglion Cells by Oral Administration of Enzyme-Treated Hesperidin The cell protection action of enzyme-treated hesperidin was studied by using a glaucoma model other than the optic nerve crush injury, that is, a model in which ganglion cell death is induced by 7N-methyl-D-aspartic acid (hereinafter referred to as "NMDA") administration.

[Materials and Method]
<Materials>
Test substance: enzyme-treated hesperidin (product name: "αG-Hesperidin PA-T", Glico Nutrition Co., Ltd.)
Animal used: C57BL/6 mice, male, 8-12 weeks old, each approximately 25 g The experiment was conducted according to the following method. The number of samples in each group was 5.
<Method>

(1) After the mice were received, the mice were habituated for one week. During this period, the mice were fed with water and feed ad lib.

(2) To the mice in the experimental group, 200 μL of phosphate-buffered saline (containing no KCl) (pH: 7.2) (Nacalai Tesque, Inc., product number: 11480-35) (hereinafter referred to as "PBS") supplemented with the enzyme-treated hesperidin at 20% (w/v) was orally administered by using an oral probe (Sonde) three times a day for 7 days; to the mice in the control group, 200 μL of PBS was administered likewise.

(3) After the 7-day oral administration, 0.3 ml of 10% Nembutal was intramuscularly administered to the thigh of each mouse for the general anesthesia.

(4) A site below the corneal limbus of the mouse was perforated with a 30-gauge needle.

(5) By using a Hamilton syringe and a 32-gauge needle, 2 μL of PBS supplemented with NMDA (Sigma-aldrich) at 15 μM was administered into the vitreous body of the mouse.

(6) The conjunctiva of the mouse was redressed, and an antibacterial ophthalmic ointment was instilled. The treatment was performed on only a single eye, and the fellow eye was untreated. The mouse was kept warm and left alone until the arousal.

(7) From the following day, 200 μL of PBS supplemented with the enzyme-treated hesperidin at 20% (w/v) was orally administered to the mice in the experimental group by using an oral probe three times a day; to the mice in the control group, 200 μL of PBS was administered likewise.

(8) To label the retinal ganglion cells, three days after the NMDA administration into the vitreous body, 1% Fluoro-Gold (Fluorochrome, LLC) was injected into the superior colliculus of the mouse brain under anesthesia.

(9) Seven days after the Fluoro-Gold labeling, cervical vertebrae of the mice were dislocated, and the eyeballs were excised. The retinas were fixed with 4% paraformaldehyde phosphate buffer solution (Wako Pure Chemical Industries, Ltd.) for 2 hours, and then washed with DPBS (Gibco, product number: 14190-144), and a fluorescent mounting agent VECTASHIELD Mounting Medium (Vector Laboratories, Product Code: H-1000) was mounted thereon.

(10) Images of 12 sites each of 500 square pixels on one retina were captured with a fluorescence microscope.

(11) The number of cells labeled with Fluoro-Gold was counted to obtain an average number at the 12 sites. This was regarded as the number of viable retinal ganglion cells per square millimeter. The average was obtained for each group.

As a result, FIG. 3 shows the ratio of the average number of viable retinal ganglion cells per square millimeter in the experimental group, given that the average number of viable retinal ganglion cells per square millimeter in the control group is taken as 1. The average number of viable retinal ganglion cells per square millimeter in the experimental group (in FIG. 3, "damage+enzyme-treated hesperidin") was larger than the average number of viable retinal ganglion cells per square millimeter of the control group. To put it differently, this test revealed that the orally administered enzyme-treated hesperidin suppressed the retinal ganglion cell death induced by NMDA.

Test 4. Study of Effect of Protecting Retinal Ganglion Cells by Intraocular Administration of Enzyme-Treated Hesperidin The cell protection action of the enzyme-treated hesperidin was studied by using the model in which ganglion cell death is induced by NMDA administration.

[Materials and Method]

<Materials>

Test substance: enzyme-treated hesperidin (product name: "αG-Hesperidin PA-T", Glico Nutrition Co., Ltd.)

Animal used:C57BL/6 mice, male, 8-12 weeks old, each approximately 25 g

The experiment was conducted according to the following method. The number of samples in each group was 4 to 6.

<Method>

(1) To the thigh of each mouse, 0.3 ml of 10% Nembutal was intramuscularly administered for the general anesthesia.

(2) A site below the corneal limbus of the mouse was perforated with a 30-gauge needle.

(3) To the mice in the experimental group, 2 μL of PBS supplemented with NMDA (Sigma-aldrich) at 15 mM and the enzyme-treated hesperidin at 17% (w/v) was administered into the vitreous bodies. On the other hand, to the mice in the control group, 2 μL of PBS supplemented with NMDA (Sigma-aldrich) at 15 mM was administered into the vitreous bodies. The treatment was performed on only single eyes of the mice, and the fellow eyes were untreated. For the administration, a Hamilton syringe and a 32-gauge needle were used.

(4) The conjunctiva of each mouse was redressed, and an antibacterial ophthalmic ointment was instilled. The mouse was kept warm and left alone until the arousal.

(5) To label the viable retinal ganglion cells, three days after the NMDA administration into the vitreous body, 2 μL of 2% Fluoro-Gold (Fluorochrome, LLC) was injected into the superior colliculus of the mouse brain under anesthesia.

(6) Seven days after the Fluoro-Gold labeling, cervical vertebrae of the mice were dislocated, and the eyeballs were excised. The retinas were fixed with 4% paraformaldehyde phosphate buffer solution (Wako Pure Chemical Industries, Ltd., Distributor Code: 163-20145) for 2 hours, and then washed with DPBS (Gibco, product number: 14190-144), and a fluorescent mounting agent VECTASHIELD Mounting Medium (Vector Laboratories, Product Code: H-1000) was mounted thereon.

(7) Images of 12 sites each of 500 square pixels on one retina were captured with a fluorescence microscope.

(8) The number of cells labeled with Fluoro-Gold was counted to obtain an average number at the 12 sites. This was regarded as the number of viable retinal ganglion cells per square millimeter. The average was obtained for each group.

Figure 4:
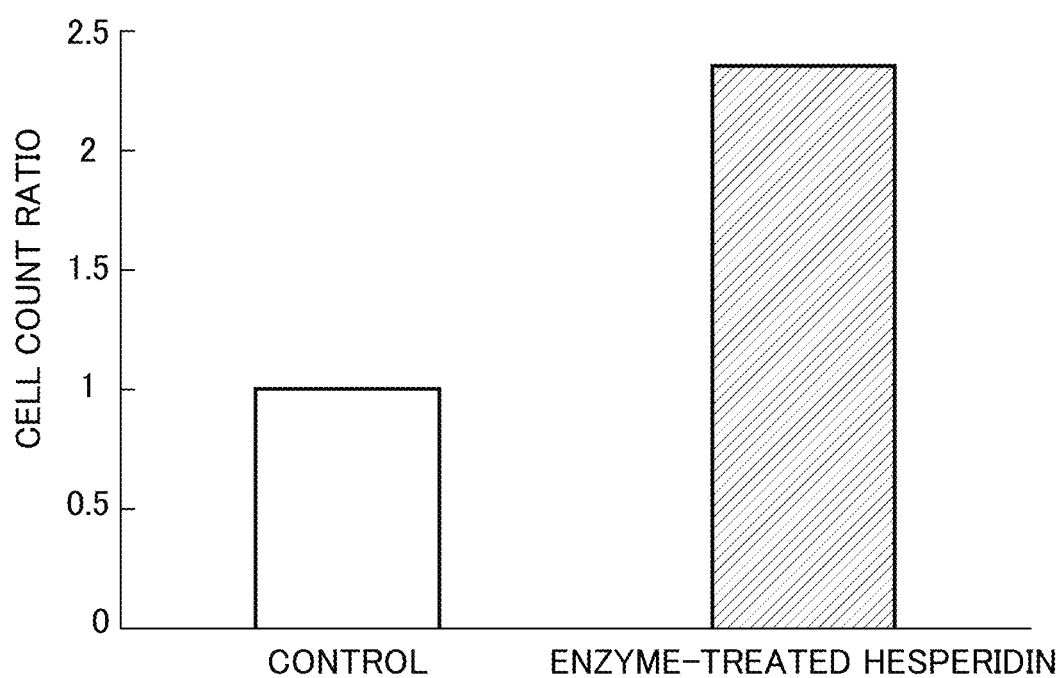
FIG. 4 shows the result of Test 4 (ratio of viable retinal ganglion cells by enzyme-treated hesperidin intraocular administration).

As a result, FIG. 4 shows the ratio of the average number of viable retinal ganglion cells per square millimeter in the experimental group, given that the average number of viable retinal ganglion cells per square millimeter of the control group is taken as 1. The average number of viable retinal ganglion cells per square millimeter in the experimental group (in FIG. 4, "enzyme-treated hesperidin") was larger than the average number of viable retinal ganglion cells per square millimeter of the control group (in FIG. 4, "control"). This test revealed that the intraocularly administered enzyme-treated hesperidin suppressed the retinal ganglion cell death induced by the NMDA administration.

Figure 5:
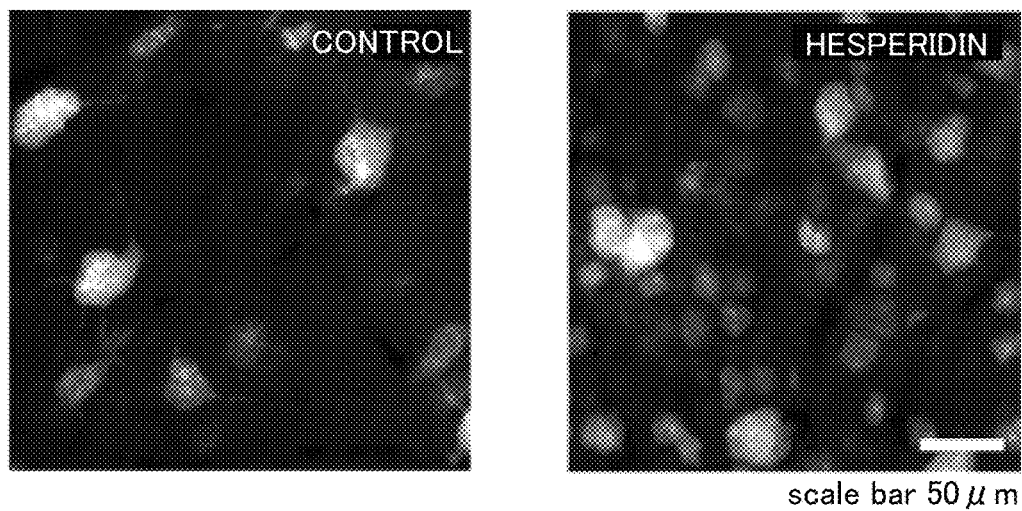
FIG. 5 shows the result of Test 4 (photographs of the viable retinal ganglion cells by the enzyme-treated hesperidin intraocular administration).

FIG. 5 shows the photographs of the viable retinal ganglion cells.

Test 5. Study of Effect of Protecting Retinal Ganglion Cells by Intraocular Administration of Enzyme-Treated Hesperidin The action of a test substance to suppress retinal ganglion cell death induced by NMDA administration was verified. Expressions of genes Rbpms, Brn3b, and Brn3c specific to retinal ganglion cells were studied by RT-PCR.

[Materials and Method]

<Materials>

Test substance: enzyme-treated hesperidin (product name: "αG-Hesperidin PA-T", Glico Nutrition Co., Ltd.)

Test animal: C57BL/6 mice, male, 8-12 weeks old, each approximately 25 g

The experiment was conducted according to the following method. The number of samples in each group was 5 or 6.

<Method>

(1) To the mice in the experimental group, 2 μL of PBS supplemented with the enzyme-treated hesperidin at 17% (w/v) and NMDA (Sigma-aldrich) at 15 mM was administered into the vitreous bodies of the right eyes by using a Hamilton syringe and a 32-gauge needle. To the mice in the control groups, 2 μL of PBS supplemented with NMDA (Sigma-aldrich) at 15 mM was administered into the vitreous bodies of the right eyes by using a Hamilton syringe and a 32-gauge needle. To the mice in an untreatment group, nothing was administered into the vitreous bodies of the right eyes.

(2) After 24 hours, cervical vertebrae of the mice were dislocated, and the eyeballs were excised. The retinas were fixed with 4% paraformaldehyde phosphate buffer solution (Wako Pure Chemical Industries, Ltd.).

(3) Using miRNeasy Mini Kit (Qiagen), Total RNAs were extracted.

(4) Using SuperScriptIII (Invitrogen), cDNAs were synthesized. As a real-time PCR, the Taqman probe assay was adopted, and thermal cycler FAST 7500 (ABI) and Master Mix (ABI) were used. All the probes were pre-designed by ABI, and the probes were purchased for use. The followings are primers used. Rbpms (Mm00803908_m1), Brn3b (Mm00454754_S1), Brn3c (Mm04213795_s1), Gapdh (Mm99999915_g1).

(5) The level of each target gene expressed was corrected by the ΔΔCt method (comparative Ct method) using Gapdh as an endogenous control for the relative quantifications. For each group, the averages and the standard deviations of the levels of the genes expressed were determined.

Figure 6:
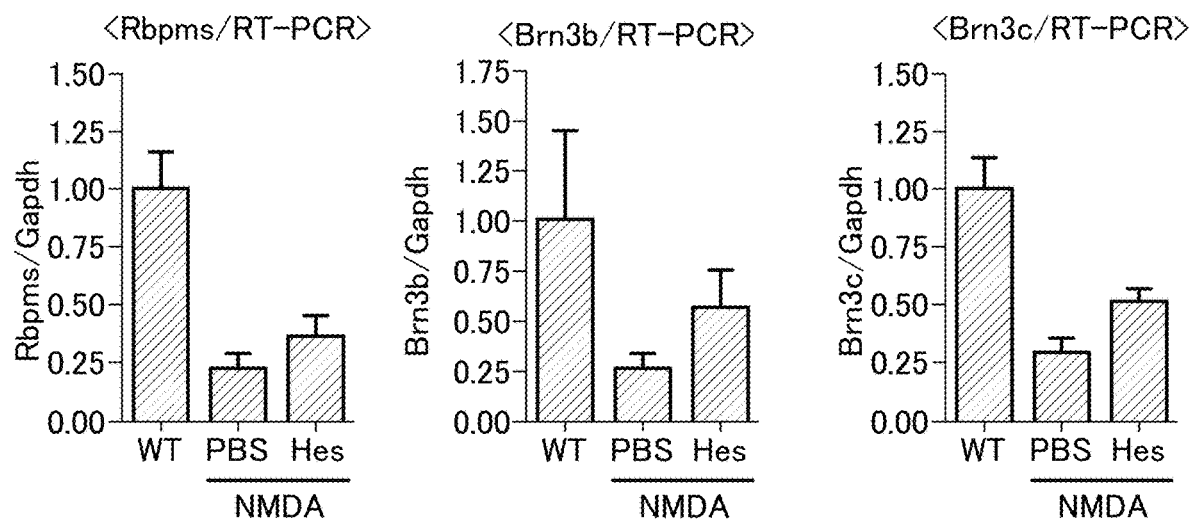
FIG. 6 shows the result of Test 5 (levels of retinal-ganglion-cell specific genes expressed by enzyme-treated hesperidin intraocular administration).

As a result, as shown in FIG. 6, the levels of the retinal-ganglion-cell specific genes Rbpms, Brn3b, and Brn3c expressed in the experimental group (in FIG. 6, "Hes") were greater than those in the control group (in FIG. 6, "PBS"). This was presumably because the enzyme-treated hesperidin suppressed the retinal ganglion cell death induced by the NMDA administration in the experimental group, so that decreases in the levels of the retinal-ganglion-cell specific genes expressed were suppressed in comparison with the control group. This test suggested the nerve protection action of the enzyme-treated hesperidin through the intraocular administration.

Test 6. Study of Effect of Protecting Retinal Ganglion Cells by Intraocular Administration of Enzyme-Treated Hesperidin The action of a test substance to suppress retinal ganglion cell death induced by NMDA administration was verified.

An anti-RBPMS antibody was used to evaluate the number of retinal ganglion cells. RBPMS is a marker protein of retinal ganglion cells.

[Materials and Method]

<Materials>

Test substance: enzyme-treated hesperidin (product name: "αG-Hesperidin PA-T", Glico Nutrition Co., Ltd.)

Test animal: C57BL/6 mice, male, 8-12 weeks old, each approximately 25 g

The experiment was conducted according to the following method. The number of samples in each group was 5 or 6.

<Method>

(1) Into the vitreous bodies of the right eyes of the mice in the experimental group, 2 μL of PBS supplemented with NMDA (Sigma-aldrich) at 15 mM and the enzyme-treated hesperidin at 17% (w/v) was administered. Into the vitreous bodies of the right eyes of the mice in the control group, 2 μL of PBS supplemented with NMDA (Sigma-aldrich) at 15 mM was administered. Into the vitreous bodies of the right eyes of the mice in the untreatment group, nothing was administered. For the administration, a Hamilton syringe and a 32G needle were used.

(2) After 24 hours, cervical vertebrae of the mice were dislocated, and the right eyeballs were excised. The retinas were fixed with 4% paraformaldehyde phosphate buffer solution (Wako Pure Chemical Industries, Ltd.).

(3) Frozen sections of the retinas were prepared through sucrose replacement and OCT embedding. The sections were washed with PBS supplemented with Tween-20 at 0.04% (v/v) (hereinafter referred to as "Tw-PBS") for 5 minutes three times.

(4) Each section was allowed to react in Tw-PBS supplemented with polyoxyethylene (10) octylphenyl ether (Wako Pure Chemical Industries, Ltd., Distributor Code: 168-11805) at 0.5% (v/v) for 10 minutes, and then washed with Tw-PBS for 5 minutes three times.

(5) A blocking solution prepared by supplementing Tw-PBS with Donkey Serum (biowest, # S2170-100) at 10% (v/v) was added in an amount of 50 μL per section, and left standing at room temperature for 1 hour.

(6) The sections were left standing at room temperature for 1 hour in a solution prepared with the aforementioned blocking solution:Anti-RBPMS antibody (Abeam ab194213)=1:200 (primary antigen reaction). Then, the sections were washed with Tw-PBS for 5 minutes three times.

(7) The sections were left standing at room temperature for 1 hour in a solution prepared with the aforementioned blocking solution:Donkey anti-Rabbit IgG (H+L) Secondary Antibody, Alexa Fluor(registered trademark) 488 conjugate (Molecular Probe, # A21206)=1:500 (secondary antigen reaction). Then, the sections were washed with Tw-PBS for 5 minutes three times.

(8) A DAPI-containing mounting agent (Vector Laboratories, product name: VECTASHIELD Mounting Medium with DAPI) was mounted on the sections, and the edges of the cover glass were fixed by top coating.

(9) Images were captured with a fluorescence microscope. The number of RBPMS-expressing cells in the entire retina was counted to obtain the average for each group. This was regarded as the number of viable retinal ganglion cells per eye.

Figure 7:
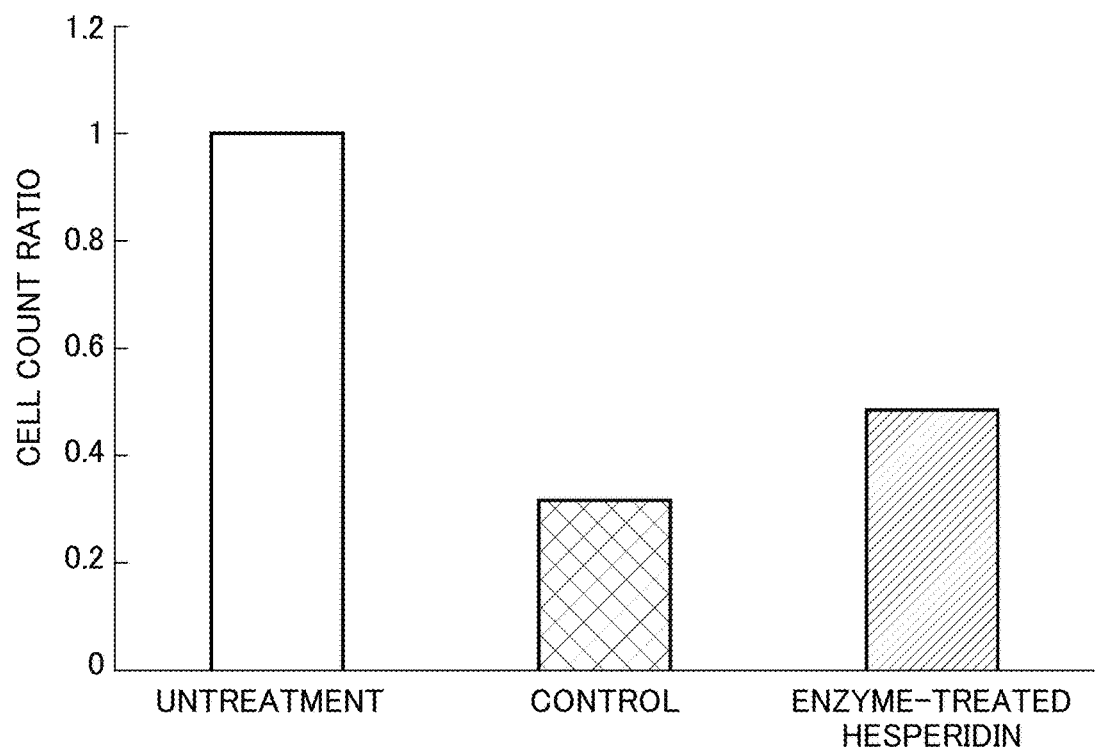
FIG. 7 shows the result of Test 6 (ratio of the number of viable RBPMS cells with enzyme-treated hesperidin).
Figure 8:
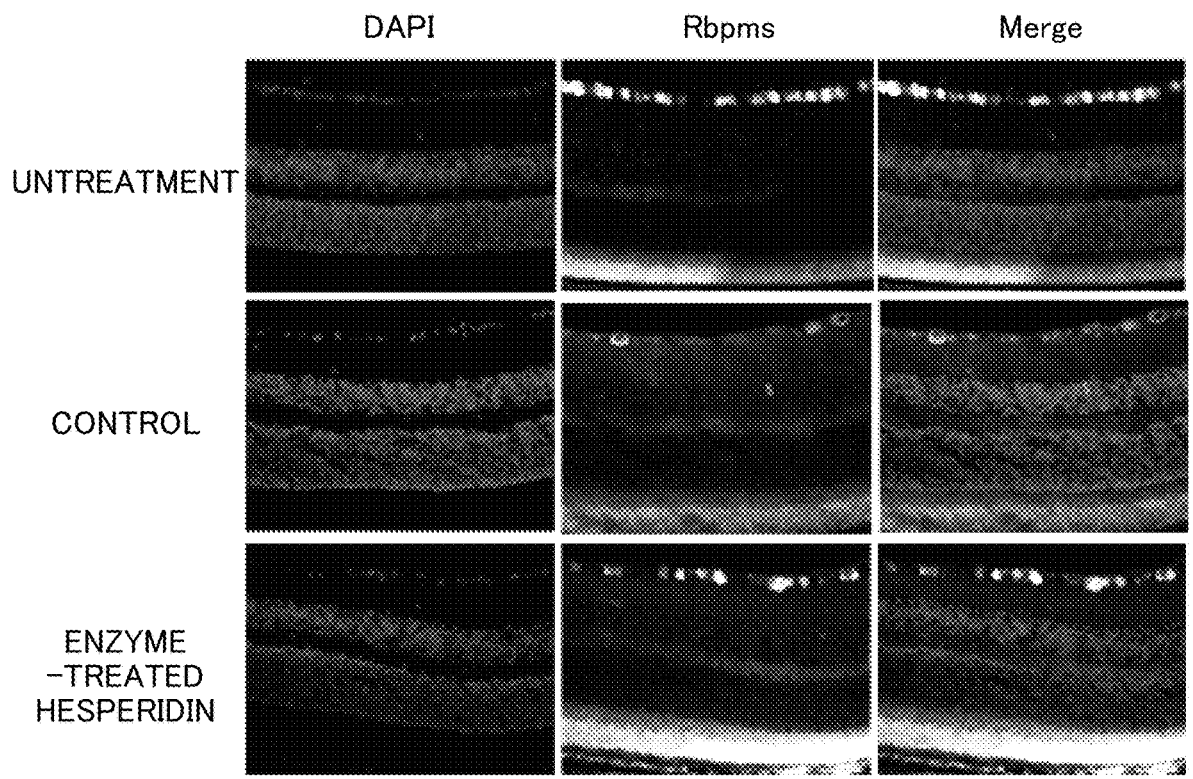
FIG. 8 shows the result of Test 6 (photographs of the RBPMS-expressing cells by enzyme-treated hesperidin intraocular administration).

As a result, FIG. 7 shows the ratios of the numbers of viable retinal ganglion cells per eye in the control group (in FIG. 7, "control") and the experimental group (in FIG. 7, "enzyme-treated hesperidin"), given that the number of viable retinal ganglion cells per eye in the untreatment group (in FIG. 7, "untreatment") is taken as 1. The number of viable retinal ganglion cells per eye in the experimental group was larger than the number of viable retinal ganglion cells per eye of the control group. This revealed that the intraocularly administered enzyme-treated hesperidin suppressed the retinal ganglion cell death induced by the NMDA administration. Additionally, FIG. 8 shows the photographs of the RBPMS-expressing cells (immunostained).

Test 7. Study of Effect of Protecting Retinal Ganglion Cells by Intraocular Administration of Enzyme-Treated Hesperidin The electrophysiological function of the enzyme-treated hesperidin was evaluated and studied by using the model in which retinal ganglion cell death is induced by NMDA administration.

[Materials and Method]

<Materials>

Test substance: enzyme-treated hesperidin (product name: "αG-Hesperidin PA-T", Glico Nutrition Co., Ltd.)

Animal used: C57BL/6 mice, male, 8-12 weeks old, each approximately 25 g

The experiment was conducted according to the following method. The number of samples in each group was 8 to 10.

<Method>

(1) Medetomidine (Meiji Co., Ltd.) at a dose of 0.6 mg/kg and ketamine (Daiichi Sankyo Company, Limited) at a dose of 36 mg/kg were intraperitoneally injected into each mouse for the anesthesia.

(2) The scalp of the mouse was cut to expose the skull. Then, microelectrodes (stainless steel pan-head screws M0.6×3.0 mm in length) were implanted therein. As the electrodes, a cathode was implanted 2 mm at the front side of the bregma, while anodes were implanted 3.6 mm at the rear side thereof respectively at right and left positions 2.3 mm from the midline. All the electrodes were implanted at a depth of 1 mm.

(3) Subsequently, polycarbonate screws for fixation were fixed to the top of the head. Finally, the skull and the heads of the screws thus exposed were covered and fixed with a dental cement (GC dental products, product name: GC Unifast III). The mouse was constantly kept warm on a heating pad during the surgery. After the completion, a medetomidine antagonist atipamezole (Meiji Seika Pharma Co., Ltd.) was intraperitoneally injected at a dose of 0.35 mg/kg for the recovery from the anesthesia.

(4) Seven days after the microelectrode implantation, 2 μL of PBS supplemented with NMDA (Sigma-aldrich) at 15 mM was administered into the vitreous bodies of the right eyes of the mice in the control group; 2 μL of PBS supplemented with NMDA (Sigma-aldrich) at 15 mM and the enzyme-treated hesperidin at 17% (v/v) was administered into the experimental group. The left eyes were untreated.

(5) Ten days after the NMDA administration, 2.5% phenylephrine and 1.0% tropicamide were administered to the eyes of the mice for the mydriasis. Then, each mouse was placed on a holder and fixed thereto with the screws at the top of the head while freely movable.

(6) The anodes were attached to right and left portions of the visual cortex of the mouse, the cathode was attached to the forehead of the mouse, and a ground electrode (earth) was attached to the tail of the mouse. These electrodes were connected to a recording system (Mayo Corporation, product name: evoked reaction recording device PuREC).

(7) The mouse was placed in such a manner that both eyes were positioned in the spherical surface of a Ganzfeld dome (Mayo Corporation, product name: Minigantsu), and stimulation light was given from an LED stimulator (Mayo Corporation, product name: LED light emitting device LS-100) to record visual evoked potentials. First, the visual evoked potentials were measured with light stimuli at intensities of −7.0, −6.0, −5.0, −4.0, −3.0, −2.0, and −1.0 log cd·s/m2 under dark adaptation. Then, the visual evoked potentials were measured under light adaptation (white light: 30 cd/m2) at 0, 0.5, 1.0, 1.5, and 2.0 log cd-s/m2. The signals were passed through a band path filter for 0.3 Hz and 50 Hz.

As a result, as shown in FIG. 9, the right eyes (in FIG. 8, "NMDA") of the control group (in FIG. 8, "control") lost the electrophysiological functions of the brains due to the retinal ganglion cell death induced by the NMDA administration, in comparison with the untreated left eyes (in FIG. 8, "untreatment"). In contrast, the right eyes (in FIG. 8, "NMDA") of the experimental group (in FIG. 8, "enzyme-treated hesperidin") kept almost the same electrophysiological functions as those of the untreated left eyes (in FIG. 8, "untreatment"). This suggested that the enzyme-treated hesperidin suppressed the retinal ganglion cell death induced by the NMDA administration.

Test 8. Study of Effect of Protecting Retinal Ganglion Cells by Intraocular Administration of Enzyme-Treated Hesperidin Visual acuities were studied by using the model in which retinal ganglion cell death is induced by NMDA administration.

[Materials and Method]

<Materials>

Test substance: enzyme-treated hesperidin (product name: "αG-Hesperidin PA-T", Glico Nutrition Co., Ltd.)

Animal used: C57BL/6 mice, male, 8-12 weeks old, each approximately 25 g

The experiment was conducted according to the following method. The number of samples in each group was 3 or 4.

<Method>

(1) Into the vitreous bodies of the right eyes of the mice in the experimental group, 2 µL of PBS supplemented with NMDA (Sigma-aldrich) at 15 mM and the enzyme-treated hesperidin at 17% (w/v) was administered; to the control group, 2 µL of PBS supplemented with NMDA (Sigma-aldrich) at 15 mM was administered. Into the vitreous bodies of the right eyes of the mice in the untreatment group, nothing was administered. For the administration, a Hamilton syringe and a 32G needle were used.

(2) On Day 11, Day 12, and Day 13 after the operation of (1), the visual acuities of the mice were measured once a day continuously for the three days to obtain an average visual acuity of each group. The visual acuities were measured by using OptoMotry (CerebralMechanics Inc.).

Figure 10:
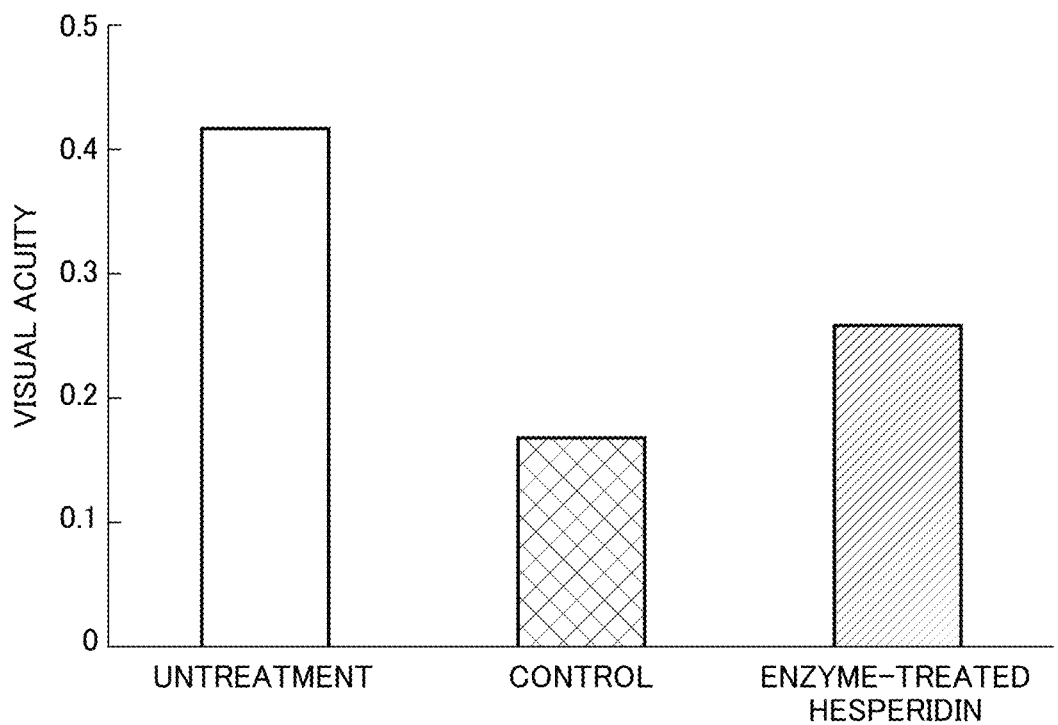
FIG. 10 shows the result of Test 8 (change in visual acuity by enzyme-treated hesperidin intraocular administration).

As a result, as shown in FIG. 10, the visual acuity result suggested that the enzyme-treated hesperidin suppressed the retinal ganglion cell death induced by the NMDA administration.

Test 9. Study of Effect of Suppressing Endoplasmic Reticulum Stress

Retinal cells in which a gene Trb3 for detecting endoplasmic reticulum stress due to tunicamycin stimulation had been introduced were stimulated with tunicamycin to study ingredients which expectedly suppress endoplasmic reticulum stress.

[Materials and Method]

<Materials>

Test substances: a product obtained by steaming and drying wheat (product name: "Koujimugi(registered trademark) ST", manufactured by Fresh Food Service Co., Ltd. (hereinafter referred to as "wheat")); wild grape (product name: "Nobudou Kansou Ekisu F", manufactured by Maruzen Pharmaceuticals Co., Ltd.); Haskap (product name: "Haskap Powder S", manufactured by Nippon Shinyaku Co., Ltd.); pomegranate seeds (product name: "Zakuro shusi Kansou Ekisu", manufactured by Ask Intercity Co., Ltd.); licorice powder (product name: "Shokuhin Genryou yo Kanzoumatsu", manufactured by Nippon Funmatsu Yakuhin Co., Ltd.); Tamarind (product name: "Indian date extract powder MF", manufactured by Maruzen Pharmaceuticals Co., Ltd.); cinnamon powder (product name: "Shokuhin Genryou yo Keihimatsu", manufactured by Nippon Funmatsu Yakuhin Co., Ltd.)

Test cells: RGC-Trb3 stable cells

Test medium: this medium was prepared by adding tunicamycin (Wako Pure Chemical Industries, Ltd.) at 2 µg/mL to DMEM (Gibco, product number: 11995-073) having been supplemented with fetal bovine serum at 10%.

<Method>

(1) The RGC-Trb3 stable cells prepared at 2.83×104 cell/300 µL in the test medium were seeded in a 24-well plate in an amount of 300 µL per well, and incubated under conditions of 37° C. and —$CO_2$ overnight.

(2) In the experimental groups, 5 mg of each test substance was added to 500 µL of the test medium for the adjustment to 1%, and then diluted to the final concentration of 0.25% with the test medium. The resulting solution was added in an amount of 75 µL per well, and cultured under conditions of 37° C. and —$CO_2$ for 24 hours. In the control group, dimethyl sulfoxide was added into DMEM to 0.5%. The resulting solution was added in an amount of 75 µL per well, and cultured under conditions of 37° C. and —$CO_2$ for 24 hours.

(3) After washing with 500 µL of DPBS (Gibco, product number: 14190-144) per well, DPBS was removed, and 700 µL of QIAzol Lysis Reagent (QIAGEN) was added. The cells in the wells were scraped with a cell scraper and collected into an Eppendorf tube.

(4) Using miRNeasy Mini Kit (QIAGEN), the RNAs were extracted. Then, cDNAs were synthesized using SuperScriptIII (Invitrogen).

(5) A real-time PCR was performed by using the SuperScriptIII First-Strand Synthesis SuperMix for qRT-PCR, TaqMan Fast Universal PCR Master Mix (2×), No AmpErase UNG, a primer mouse Trb3 (Life Technologies, Mm00454879_m1), and a Gapdh primer (Life Technologies, Mm99999915_g1).

(6) The level of Trb3 expressed was corrected by the ΔΔCt method (comparative Ct method) using Gapdh as an endogenous control for the relative quantification (in each group, n=4). For each of the control group and the seven experimental groups, the average level of Trb3 expressed was determined.

Figure 11:
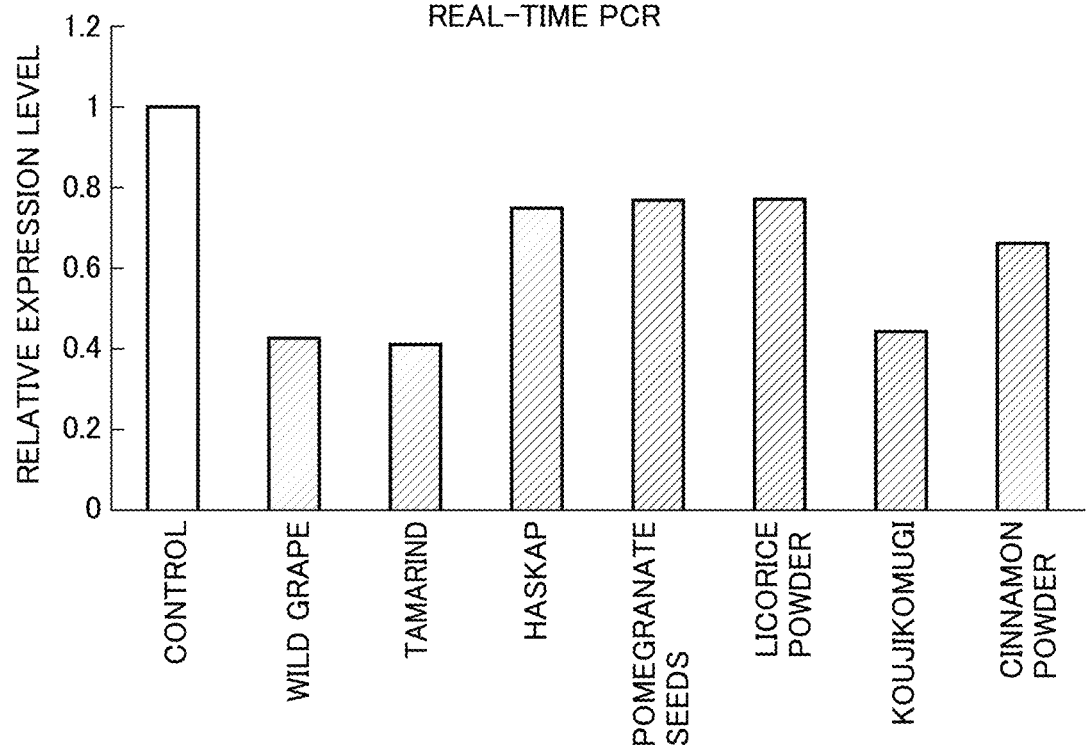
FIG. 11 shows the result of Test 9 (ratio of Trb3 expression level with each ingredient).

As a result, FIG. 11 shows the relative value of the average level of Trb3 expressed in each of the seven experimental groups, given that the average level of Trb3 expressed in the control group is taken as 1. In all of the seven experimental groups, the average levels of Trb3 expressed were lower than that of the control group. This revealed that since Trb3 is a gene whose expression is induced by endoplasmic reticulum stress, the experimental groups had an effect of suppressing endoplasmic reticulum stress. Thus, it was suggested that all of the test substances have an optic nerve protection action.

---

Identification of Deposit

| | |
|---|---|
| Name of depositary institution | National Institute of Technology and Evaluation, International Patent Organism Depositary (NITE-IPOD) |

| Identification of Deposit | |
|---|---|
| Address of depositary institution | #120, 2-5-8, Kazusakamatari, Kisarazu-shi, Chiba 292-0818, Japan |
| Date of deposit | Aug. 14, 2000 (14.08.2000) |
| Accession Number | IPOD FERM BP-7792 |

The invention claimed is:

1. A method for treating glaucoma, comprising administrating at least one active ingredient selected from the group consisting of hesperidin and Tamarind to a subject in need thereof.

2. The method according to claim 1, wherein the at least one active ingredient is administered in an amount of 0.0001 to 3.3 g per administration for a body weight of the subject of approximately 60 kg.

3. The method according to claim 1, wherein the at least one active ingredient is administered in an amount of 0.0003 to 10 g per day for a body weight of the subject of approximately 60 kg.

4. The method according to claim 1, wherein the at least one active ingredient is administered orally or intraocularly.

5. The method according to claim 1, wherein the at least one active ingredient is in the form of food or pharmaceutical product.

6. The method according to claim 1, wherein the at least one active ingredient is administered every day.

7. A method for protecting nerve cells, comprising administering an effective amount of at least one active ingredient selected from the group consisting of hesperidin and Tamarind to a subject in need thereof for protecting nerve cells of the subject.

8. The method according to claim 7, wherein the at least one active ingredient is administered in an amount of 0.0001 to 3.3 g per administration for a body weight of the subject of approximately 60 kg.

9. The method according to claim 7, wherein the at least one active ingredient is administered in an amount of 0.0003 to 10 g per day for a body weight of the subject of approximately 60 kg.

10. The method according to claim 7, wherein the at least one active ingredient is administered orally or intraocularly.

11. The method according to claim 7, wherein the at least one active ingredient is in the form of food or pharmaceutical product.

12. The method according to claim 7, wherein the at least one active ingredient is administered every day.

13. A method for suppressing optic nerve cell death, suppressing retinal ganglion cell death, or delaying a progression of visual acuity loss of human, comprising administrating at least one active ingredient selected from the group consisting of hesperidin and Tamarind to a subject in need thereof.

14. The method according to claim 13, wherein the at least one active ingredient is administered in an amount of 0.0001 to 3.3 g per administration for a body weight of the subject of approximately 60 kg.

15. The method according to claim 13, wherein the at least one active ingredient is administered in an amount of 0.0003 to 10 g per day for a body weight of the subject of approximately 60 kg.

16. The method according to claim 13, wherein the at least one active ingredient is administered orally or intraocularly.

17. The method according to claim 13, wherein the at least one active ingredient is in the form of food or pharmaceutical product.

18. The method according to claim 13, wherein the at least one active ingredient is administered every day.

* * * * *